United States Patent [19]

Germaine et al.

[11] 4,395,579

[45] Jul. 26, 1983

[54] LI-SPINEL CATALYST FOR NON-OXIDATIVE DEHYDROGENATION PROCESS

[75] Inventors: Gilbert R. Germaine; Jean P. Darnanville, both of Grand Couronne, France

[73] Assignee: Shell Oil Company, Houston, Tex.

[21] Appl. No.: 439,150

[22] Filed: Nov. 4, 1982

Related U.S. Application Data

[62] Division of Ser. No. 333,007, Dec. 21, 1981, Pat. No. 4,372,879.

[30] Foreign Application Priority Data

Dec. 29, 1980 [FR] France ................................ 80 27673

[51] Int. Cl.³ .......................... C07C 2/64; C07C 5/09; C07C 5/333
[52] U.S. Cl. .................................... 585/444; 585/445; 585/629; 585/630; 585/631; 585/661; 585/662; 585/663

[58] Field of Search ............... 585/444, 445, 629, 630, 585/631, 661, 662, 663

[56] References Cited

U.S. PATENT DOCUMENTS

| | | | |
|---|---|---|---|
| 3,626,021 | 12/1971 | Michaels et al. | 585/663 |
| 3,960,776 | 6/1976 | Ellis et al. | 585/445 |
| 4,172,854 | 10/1979 | Ellis et al. | 585/445 |
| 4,220,560 | 9/1980 | Anquetil et al. | 585/661 |

*Primary Examiner*—Curtis R. Davis

[57] ABSTRACT

The preparation of a compound of formula $R^1-C(R^2)=CH_2$ ($R^1$ and $R^2$ are a phenyl, alkyl or alkenyl group or a hydrogen atom) by contacting a mixture of steam and a compound of formula $R^1-C(R^2)(H)-CH_3$ at elevated temperature under non-oxidative dehydrogenation conditions with a catalyst having a spinel structure allows lower ratios steam to compound of formula $R^1-C(R^2)(H)-CH_3$, a higher selectivity to the compound of formula $R^1-C(R^2)=CH_2$ and a lower temperature when lithium is present in the spinel structure.

19 Claims, No Drawings

LI-SPINEL CATALYST FOR NON-OXIDATIVE DEHYDROGENATION PROCESS

This is a division, of application Ser. No. 333,007, filed Dec. 21, 1981 now U.S. Pat. No. 4,372,879.

FIELD OF THE INVENTION

This invention relates to improved catalysts for the non-oxidative dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more-saturated aliphatic hydrocarbons. This invention particularly relates to catalysts for the non-oxidative dehydrogenation of ethylbenzene to styrene.

BACKGROUND OF THE INVENTION

This invention relates to a process for the preparation of a compound having the general formula:

wherein $R^1$ and $R^2$ each represent an alkyl, an alkenyl or a phenyl group or a hydrogen atom, by non-oxidative dehydrogenation of a compound having the general formula:

wherein $R^1$ and $R^2$ have the same meaning as in formula I, in which process a mixture comprising a compound of formula II and super-heated steam is contacted at elevated temperature with a catalyst having a spinel structure. The invention also relates to novel compositions and to a process for the preparation of these compositions.

A non-oxidative dehydrogenation is a dehydrogenation whereby no molecular oxygen is added.

An important compound of formula I, styrene, is commercially prepared by dehydrogenation of ethylbenzene in the presence of a catalyst based largely on iron oxide.

A higher conversion of the compounds of formula II and a higher selectivity to the compounds of formula I - compared with the conventional iron oxide catalyst - are achieved in the presence of a catalyst having a spinel structure and containing an alkali metal oxide as promotor, see Canadian Pat. No. 1,072,987. As examples of alkali metal oxides those of sodium, potassium and cesium are mentioned.

A still higher selectivity to the compounds of formula I at the same conversion of the compounds of formula II is achieved in the presence of a spinel catalyst containing an alkali metal oxide and vanadium oxide as promotors, see U.S. Pat. No. 4,220,560, issued Sept. 2, 1980. As examples of alkali metal oxides those of sodium, potassium and cesium are mentioned.

U.S. Pat. No. 3,998,757, issued Dec. 21, 1976, and U.S. Pat. No. 4,067,922 issued Jan. 10, 1978, disclose the use of lithium spinels for use in oxidative dehydrogenation processes. U.S. Pat. No. 3,798,178, issued Mar. 19, 1974, discloses the addition of alkali metal compounds, including lithium to an unsupported iron oxide combined with a finely divided metal such as iron which provides electrical conductivity. There is no mention in this reference of spinel formation. In fact, if the catalyst of this reference were heated to a sufficiently high temperature to cause spinel formation, the metal component of the catalyst would be oxidized, destroying the desired high electrical conductivity.

The selectivity to a certain compound, expressed in a percentage, is defined as $$a/b \times 100$$

wherein "a" is the amount of the compound of formula II that has been converted into that certain compound and "b" is the total amount of the compound of formula II that has been converted.

The above known processes may be carried out in the presence of from 2 to 20 mol of steam per mol of starting compound of formula II, typically for example of 12 mol/mol.

A process has now been found which gives even higher selectivities to the compounds of formula I (at the same conversion) than the process described in U.S. Pat. No. 4,220,560, but at considerably a lower ratio of steam to the starting compound of formula II and at a lower temperature. Hence, a corresponding reduction in steam costs has been achieved.

SUMMARY OF THE INVENTION

The instant invention provides a process for the preparation of a compound having the general formula:

wherein $R^1$ and $R^2$ each represent an alkyl, an alkenyl or a phenyl group or a hydrogen atom, by non-oxidative dehydrogenation of a compound having the general formula:

wherein $R^1$ and $R^2$ each have the same meaning as in formula I, in which process a mixture comprising a compound of formula II and superheated steam is contacted at elevated temperature with a catalyst having a spinel structure, characterized in that the catalyst utilized contains lithium in the spinel structure.

The invention further relates to a composition having a spinel structure with lithium in the spinel structure, said composition being useful for non-oxidative dehydrogenation processes. Particularly, the invention relates to spinel compositions having lithium in the spinel structure and an alkali metal oxide and a vanadium oxide outside the spinel structure. The instant invention also relates to a process for the preparation of the aforementioned compositions.

The instant compositions in their use as non-oxidative dehydrogenation catalysts provide advantages of high selectivities, and high activities (lower reaction temperatures) when compared to the prior art catalysts. A particularly desirable advantage of the instant compositions is that they can be operated at low steam to starting compound ratios, lower, for example, that commercially utilized catalysts, thus providing for lower steam consumption, resulting in lower energy costs.

DESCRIPTION OF THE ILLUSTRATIVE EMBODIMENTS

The term "spinel catalyst" refers to the members of a group of multiple oxides having the same crystalline structure as the specific mineral spinel, $MgAl_2O_4$. The general formula of the spinel structure can be written $$M\frac{VI}{2}[T^{IV}O_4],$$

where the Roman numerals indicate the coordination numbers: The M-atoms are octahedrally coordinated and the T-atoms are tetrahedrally coordinated. The spinels may involve divalent (2+) and trivalent (3+) cations. Normal spinels, in which the divalent cations occupy the tetrahedral positions and the trivalent cations the octahedral positions and inverse spinels, in which the trivalent cations occupy the tetrahedral positions and equally apportioned divalent and trivalent cations the octahedral positions may be used in the process according to the present invention. The catalysts used in the present process, for example those containing iron, contain lithium in the spinel structure, the lithium atoms are octahedrally coordinated. The substitution of chromium in the spinel structure causes the lithium atoms to be displaced to the tetrahedral position. These catalysts may further contain iron, aluminum, chromium, cobalt and/or gallium as examples of trivalent metal atoms and calcium, magnesium, zinc, manganese, iron, nickel, cobalt and/or cadmium as examples of divalent metal atoms in the spinel structure. The catalyst may contain titanium, e.g. the spinel $Li_4Ti_5O_{12}$ may be used. The presence of sodium, silver and copper ions in the spinel structure is not excluded. Spinels obtained by substitution of iron by lithium in $Fe_3O_4$ may be used, for example $Li_{0.5}Fe_{2.5}O_4$ or $Li_{1.5}Fe_{2.5}O_4$. Very good results have been obtained with catalysts containing lithium and iron and with catalysts containing lithium and chromium in the spinel structure. The best results have been obtained with catalysts containing lithium, iron and chromium in the spinel structure. Other examples of spinel structures which may be present in the catalyst are those containing lithium and aluminum (for example $Li_{0.5}Al_{2.5}O_4$), lithium and chromium (for example $LiCr_5O_8$), lithium, iron and aluminum (for example $Li_{0.5}Fe_1Al_{1.5}O_4$), sodium, lithium and iron (for example $Na_{0.15}Li_{0.35}Fe_{2.5}O_4$) and lithium, iron and manganese (for example $Li_{0.5}Fe_{2.35}Mn_{0.15}O_4$) in the spinel structure, and mixtures thereof.

The spinel structure in the catalyst preferably has a molar ratio:
(a) Lithium to oxygen in the range of from about (0.01 to 3):4 and preferably from about (0.1 to 1.5):4,
(b) iron to oxygen in the range of from about (0.01 to 2.9):4 and preferably from about (1 to 2.5):4 and
(c) chromium to oxygen in the range of from about (0.01 to 2.5):4 and preferably from about (0.05 to 1):4.

Very good results have been obtained with spinel structures having the formula $Li_{0.5}Fe_{2.5}O_4$ and particularly with $Li_{0.5}Fe_{2.4}Cr_{0.1}O_4$.

The conversion of the compounds of formula II and the selectivity to the compound of formula I are enhanced by using the catalysts in question promoted with one or more alkali metal oxides, i.e. with oxides of lithium, sodium, potassium, rubidium and/or cesium. Very good results have been obtained with potassium oxide. The alkali metal oxide is suitably present in an amount in the range of from about 0.1 to about 20% by weight, calculated as oxide on the total weight of the catalysts. These promotors do not form part of the spinel structure; lithium forms part of the spinel structure and, simultaneously, other lithium atoms may be present as oxide on this structure as a promotor.

A still higher selectivity to the compound of formula I at the same high conversion of the compound of formula II is obtained by using the catalysts in question promoted with vanadium oxide, particularly with an alkali metal oxide and with vanadium oxide. The vanadium oxide is suitably present in an amount in the range of from 0.1 to 10% by weight and preferably from about 1 to about 5% by weight, calculated as $V_2O_5$ on the total weight of the catalysts. The vanadium does not form part of the spinel structure.

$R^1$ in the general formula II may represent a phenyl group carrying one or more methyl groups as substituents. Preferably, $R^1$ represents an unsubstituted phenyl group and $R^2$ a hydrogen atom or a methyl group. Very good results have been obtained with ethylbenzene as the starting compound. The alkanes of formula II preferably have in the range of from 2 to about 20 and particularly about 3 to about 8 carbon atoms per molecule; examples are n-butane and 2-methylbutane. The alkenes of formula II preferably have in the range of from about 4 to about 20 and particularly about 4 to about 8 carbon atoms per molecule; examples are 1-butane (forming 1,3-butadiene) and 2-methyl-1-butene and 3-methyl-1-butene, both forming isoprene. It is possible to convert n-butane with the present process via 1-butane into 1,3-butadiene and 2-methylbutane via tert.-amylenes into isoprene.

The process is suitably carried out using a molar ratio of steam to compound of formula II in the range of from about 2 to about 20 and preferably of from about 5 to about 13. An attractive feature of the present process is that relatively low molar ratios of steam to compound of formula II can be used, particularly in the range of from about 7.5 to about 10.

The process is suitably carried out at a temperature in the range of from about 400° C. to about 750° C. An attractive feature of the present process is that relatively low temperatures can be used, particularly in the range of from about 550° C. to about 650° C., particularly from about 600° C. to about 635° C.

The process may be carried out at atmospheric, super- or subatmospheric pressure. Atmospheric pressure is usually very suitable.

The process is suitably carried out using a liquid hourly space velocity in the range of from about 0.1 to about 5.0 l/l.h, using, for example, a tubular or radial flow reactor.

The novel compositions referred to hereinbefore have a spinel structure with lithium in the spinel structure and are characterized in that the composition also contains an alkali metal oxide and/or vanadium oxide not forming part of the spinel structure, with the proviso that the composition has a surface area less than about 8 m²/g when the only constituent of the composition which does not form part of the spinel structure is lithium oxide.

Catalysts containing lithium in the spinel structure may be prepared in any suitable manner, for example by intimately mixing the starting metal compounds and heating the mixture obtained to a temperature sufficiently high to produce the required spinel structure, for example to a temperature between about 700° C. and about 1000° C.

Examples of starting metal compounds are oxides, hydroxides and salts, for example nitrates, oxalates, carbonates, acetates, formates and halides. Catalysts showing a particularly high activity are prepared by fusing lithium nitrate with the nitrate(s) of the metal(s) destined to form part of the spinel structure, drying the mixture obtained and heating the dried mixture to a temperature sufficiently high to cause formation of a spinel structure and bringing an alkali metal oxide and/or vanadium oxide onto the spinel structure.

The following Examples further illustrate the invention but are being provided for illustrative purposes only and are not intended to limit the scope of the invention. The catalysts used in these examples gave an X-ray diffraction pattern revealing a spinel structure with lithium and iron in the spinel structure according to ASTM 17.114. Potassium and vanadium did not form part of the spinel structure.

Preparation of Catalysts 1, 2 and 4

Hereafter the preparation of catalyst 1 is given. Catalysts 2 and 4 were prepared in the same manner.

$Li_2CO_3$ (0.5 mol), hydrated $Fe_2O_3$ (4.6 mol $Fe_2O_3$ containing 84.1% $Fe_2O_3$), $Fe(NO_3)_3.9H_2O$ (0.2 mol) and $Cr(NO_3)_3.9H_2O$ (0.2 mol) were ground together, the mixture formed was gradually heated to a temperature of 800° C. for 24 hours and then allowed to adopt ambient temperature. The crystals thus obtained had the formula $Li_{0.5}Fe_{2.4}Cr_{0.1}O_4$.

The above crystals (100 g), $NH_4VO_3$ (4.6 g), potassium alginate (5 g), water (19 g) containing $K_2CO_3$ (19.3 g) and sorbitol (0.75 g) were thoroughly mixed and the mass obtained was extruded and pelletized to obtain cylindrical particles with a diameter of 3 mm and a length of 5 mm. The pellets were dried for 12 hours at 120° C., calcined for 2 hours at 800° C. and then allowed to adopt ambient temperature. The catalyst obtained had the formula $Li_{0.5}Fe_{2.4}Cr_{0.1}O_4$ containing 12% w of $K_2O$ and 3% w of $V_2O_5$, both calculated on the total composition.

Preparation of Catalyst 3

$LiNO_3$ (1 mol), $Fe(NO_3)_3.9H_2O$ (4.8 mol) and $Cr(NO_3)_3.9H_2O$ (0.2 mol) were fused together above a boiling water bath and the mixture thus formed was kept above the bath to evaporate the water slowly until the mass was dry. The dried mixture was gradually heated to a temperature of 800° C. for 24 hours and then allowed to adopt ambient temperature. The crystals thus obtained had the same formula as catalyst 1.

The promotors potassium and vanadium were brought onto these crystals in the manner described for catalysts 1, 2 and 4.

Some physical data of the four catalysts are given in Table 1.

TABLE 1

| Catalyst No. | Composition Spinel | $K_2O$ % w | $V_2O_5$ % w | Bulk Density g/cm³ | Surface Area m²/g |
|---|---|---|---|---|---|
| 1 | $Li_{0.5}Fe_{2.4}Cr_{0.1}O_4$ | 12 | 3 | 1.44 | 1.0 |
| 2 | $Li_{0.5}Fe_{2.5}O_4$ | 12 | 3 | 1.4 | 1.4 |
| 3 | $Li_{0.5}Fe_{2.4}Cr_{0.1}O_4$ | 12 | 3 | 1.3 | below 1 |
| 4 | $Li_{0.5}Fe_{2.4}Cr_{0.1}O_4$ | 12 | 1.5 | 1.3 | 2.0 |

The experiments described below had the following in common.

A mixture of steam and ethylbenzene, heated to a temperature of 600° C., was introduced at the top of an externally heated, vertically positioned, cylindrical reactor having an internal diameter of 2.7 cm and charged with catalyst (100 ml). The mixture was conducted at a pressure of 1 bar and using a liquid hourly space velocity for ethylbenzene of 0.65 l/l.h through the catalyst bed.

The reaction product leaving the reactor was cooled to a temperature of 20° C. and the liquid condensed thereby was analyzed by means of gas-liquid chromatography. From the data obtained the conversion of ethylbenzene and the selectivity to styrene were calculated.

EXAMPLES 1–8

The catalysts 1, 2, 3 and 4 were tested in 8 experiments using the molar steam/ethylbenzene ratios stated in Table 2 and adjusting the temperature of the catalyst bed until the conversion of the ethylbenzene was 70%; this temperature is indicated as "T(70)". Table 2 also states the duration of each experiment and presents the values for T(70) and the selectivities to styrene at 70% conversion (indicated as "S(70)").

TABLE 2

| Catalyst No. | Composition | Example No. | Steam/ethylbenzene Ratio m/m | Duration h | T(70) °C. | S(70) % | Example No. | Steam/ethylbenzene Ratio m/m | Duration h | T(70) °C. | S(70) % |
|---|---|---|---|---|---|---|---|---|---|---|---|
| 1 | $Li_{0.5}Fe_{2.4}Cr_{0.1}O_4$ $12K_2O/3V_2O_5$ | 1 | 12 | 230 | 623 | 96.8 | 2 | 9.3 | 290 | 623 | 96.6 |
| 2 | $Li_{0.5}Fe_{2.5}O_4$ $12K_2O/3V_2O_5$ | 3 | 12 | 200 | 621 | 96.1 | 4 | 8.9 | 260 | 621 | 96.1 |
| 3 | $Li_{0.5}Fe_{2.4}Cr_{0.1}O_4$ $12K_2O/3V_2O_5$ | 5 | 12 | 160 | 614 | 96.7 | 6 | 9.6 | 280 | 613 | 96.8 |
| 4 | $Li_{0.5}Fe_{2.4}Cr_{0.1}O_4$ $12K_2O/1.5V_2O_5$ | 7 | 12 | 150 | 615 | 96 | 8 | 9.2 | 150 | 616 | 95.3 |

Table 2 shows that a decrease in the steam/ethylbenzene ratio from 12 to about 9 hardly influences or does not influence at all the temperature to obtain 70% conversion and the selectivity to styrene, compare examples 1 and 2, examples 3 examples 5 and 6 and examples 7 and 8. The table alsow shows that a catalyst prepared by fusing the starting nitrates is more active than a catalyst prepared by starting from carbonates and oxides, at the same high selectivity to styrene, compare the temperatures of examples 1 and 5 and those of examples 2 and 6.

None of the catalysts exhibited any deactivation at the end of the experiments.

The chromium-free catalyst was as active and stable as the chromium-containing catalyst, but the selectivity to styrene of the latter was slightly higher, compare examples 1 and 3 and examples 2 and 4.

Examples 6 was prolonged by decreasing the steam/ethylbenzene ratio to 7.5 and the temperature to 571° C. This resulted in a selectivity to styrene of more than 99% at 44% ethylbenzene conversion.

An increase in the $V_2O_5$ content from 1.5 to 3% w results in an increase in the selectivity to styrene, compare examples 1 and 7 and examples 2 and 8.

EXAMPLES 9 and 10 and Comparative Experiments A, B and C

Three catalysts were prepared in the same manner as catalyst 3, starting from the metal nitrates. Some physical data on these catalysts are stated in Table 3

TABLE 3

| Catalyst | | $K_2O$ % w | $V_2O_5$ % w | Bulk Density g/cm³ | Surface area m²/g |
|---|---|---|---|---|---|
| No. | Composition | | | | |
| 5 | $Li_{0.5}Fe_{2.4}Cr_{0.1}O_4$ | 12 | 3 | 1.34 | less than 1 |
| 6 | $CaFe_{1.9}Cr_{0.1}O_4$ | 12 | 3 | 1.37 | less than 1 |
| 7 | $MgFe_{1.9}Cr_{0.1}O_4$ | 12 | 3 | 1.25 | 1.6 |

The catalysts 5, 6 and 7 were tested in 5 experiments in the manner described in Examples 1–8.

Table 4 presents the results obtained after 500 hours' operation.

TABLE 4

| Catalyst No. | Composition | Example No. | Steam/ ethylbenzene m/m | T(70) °C. | S(70) % | Example No. | Steam/ ethylbenzene m/m | T(70) °C. | S(70) % |
|---|---|---|---|---|---|---|---|---|---|
| 5 | $Li_{0.5}Fe_{2.4}Cr_{0.1}O_4$ 12 $K_2O$/3 $V_2O_5$ | 9 | 12 | 614 | 96.5 | 10 | 9 | 614 | 96.4 |
| | | Comparative Experiment | | | | Comparative Experiment | | | |
| 6 | $CaFe_{1.9}Cr_{0.1}O_4$ 12 $K_2O$/3 $V_2O_5$ | | | | | A | 9 | 630[1] | 95.3 |
| 7 | $MgFe_{1.9}Cr_{0.1}O_4$ 12 $K_2O$/3 $V_2O_5$ | B | 12 | 613 | 94.8 | C | 9 | 627 | 94.2 |

[1] Conversion 56.6% instead of 70%.

Table 4 shows that: (1) at a steam/ethylbenzene ratio of 12 catalyst 5 (according to the invention) gives a higher selectivity to styrene than catalyst 7 (not according to the invention) at about the same value for T(70), compare Example 9 with Comparative Experiment B; (2) at a steam/ethylbenzene ratio of 9 catalyst 5 (according to the invention) gives a considerably higher selectivity to styrene at a considerably lower T(70) value than catalyst 7 (not according to the invention); (3) at a steam/ethylbenzene ratio of 9 catalyst 5 (according to the invention) gives a considerably higher selectivity to styrene than catalyst 6 (not according to the invention) at a much lower T(70) value than the temperature required for catalyst 6 to obtain only 56.6% conversion.

We claim:

1. A process for the preparation of a compound having the general formula:

(I)

wherein $R^1$ and $R^2$ each represent an alkyl, an alkenyl or a phenyl group or a hydrogen atom, by non-oxidative dehydrogenation of a compound having the general formula:

(II)

wherein $R^1$ and $R^2$ have the same meaning as in formula I, in which process a mixture comprising a compound of formula II and superheated steam is contacted at elevated temperature with a catalyst comprising a composition having a spinel structure with lithium coordinated in the spinel structure, an alkali metal oxide not forming a part of the spinel structure and a vanadium oxide not forming part of the spinel structure.

2. The process of claim 1 wherein the spinel structure also contains iron.

3. The process of claim 1 wherein the spinel structure also contains chromium.

4. The process of claim 2 wherein the spinel structure also contains chromium.

5. The process of claim 2 wherein the spinel structure has a molar ratio of iron to oxygen ranging from about 1:4 to about 2.5:4.

6. The process of claim 4 wherein the spinel structure has a molar ratio of iron to oxygen ranging from about 1:4 to about 2.5:4.

7. The process of claim 3 wherein the spinel structure has a molar ratio of chromium to oxygen ranging from about 0.05:4 to about 1:4.

8. The process of claim 4 wherein the spinel structure has a molar ratio of chromium to oxygen ranging from about 0.05:4 to about 1:4.

9. The process of claims 1, 2, 3, 4, 5, 6, 7, or 8 wherein the spinel structure has a molar ratio of lithium to oxygen ranging from about 0.1:4 to about 1.5:4.

10. The process of claim 1 wherein the spinel structure has the approximate formula $Li_{0.5}Fe_{2.4}Cr_{0.1}O_4$.

11. The process of claim 1 wherein the spinel structure has the approximate formula $Li_{0.5}Fe_{2.5}O_4$.

12. The process of claim 1 wherein the alkali metal is present in an amount ranging from about 0.1 to about 20 percent by weight, calculated as the oxide on the total weight of the catalyst and the vanadium oxide is present in an amount ranging from about 0.1 to about 10 percent by weight, calculated as $V_2O_5$ on the total weight of the catalyst.

13. The process of claim 1 wherein the alkali metal oxide is lithium oxide and the surface area of the catalyst is less than about 8 m²/g.

14. The process of claim 1 wherein a molar ratio of steam to compound of formula II ranging from about 5 to about 13 is used.

15. The process of claim 14 wherein the molar ratio of steam to compound II ranges from about 7.5 to about 10.

16. The process of claim 1 wherein the dehydrogenation is carried out at a temperature ranging from about 400° C. to about 750° C.

17. The process of claim 16 wherein the temperature ranges from about 550° C. to about 650° C.

18. The process of claim 17 wherein the temperature ranges from about 600° C. to about 635° C.

19. The process of claim 1 wherein the alkali metal oxide is potassium oxide.

* * * * *